United States Patent
Mai et al.

(10) Patent No.: US 6,790,984 B1
(45) Date of Patent: Sep. 14, 2004

(54) PROCESS FOR PURIFYING PRAVASTATIN SODIUM FROM A FERMENTATION BROTH

(75) Inventors: Jing-Chen Mai, Taoyuan Hsien (TW); Chiou-Jour Laih, Taipei Hsien (TW); Yu-Chin Chiang, Taichung Hsien (TW)

(73) Assignee: Chunghwa Chemical Synthesis & Biotech Co., Ltd., Taipei Hsien (TW)

( * ) Notice: Subject to any disclaimer, the term of this patent is extended or adjusted under 35 U.S.C. 154(b) by 0 days.

(21) Appl. No.: 10/439,802

(22) Filed: May 14, 2003

(30) Foreign Application Priority Data

Feb. 21, 2003 (TW) .................................. 92103727 A

(51) Int. Cl.⁷ .............................................. C07C 67/02

(52) U.S. Cl. ...................................................... 560/256

(58) Field of Search ......................................... 560/256

(56) References Cited

FOREIGN PATENT DOCUMENTS

EP          1327626      *   4/2002

\* cited by examiner

*Primary Examiner*—Paul J. Killos

(57) ABSTRACT

A process for purifying pravastatin sodium comprising the steps of:

a. clarifying a fermentation broth containing pravastatin sodium to obtain a clear solution; and adjusting the clear solution to be basic having pH value ranging from pH 10~13;

b. adsorbing the pravastatin sodium with non-ionic resin; eluting the pravastatin sodium by water-soluble organic solvent; and forming a concentrate of pravastatin sodium;

c. treating the concentrate with water-soluble anti-solvent or inorganic salt to form a precipitate of pravastatin sodium; and d. recrystallizing the precipitate for making pravastatin sodium crystal with high purity and high yield.

5 Claims, No Drawings

PROCESS FOR PURIFYING PRAVASTATIN SODIUM FROM A FERMENTATION BROTH

BACKGROUND OF THE INVENTION

U.S. Pat. No. 4,346,227 to Terahara et al. disclosed a pravastatin which can be obtained by fermentation of compactin using a variety of microorganisms. After fermentation, pravastatin was separated from the fermentation broth by acidifying the broth to a pH of 3 and extracting pravastatin and other non-hydrophilic organics with ethyl acetate, followed by washing with brine. The pravastatin free acid was lactonized by addition of a catalytic amount of trifluoroacetic acid, then neutralized with dilute sodium bicarbonate, dried over sodium sulfate and evaporated to dryness. The residue was purified by preparative reverse-phase high performance liquid chromatography. However, such a reverse-phase HPLC is not an economical method of purification for large-scale preparation of a chemical compound as evaluated by those skilled in the art.

Meanwhile, the pravastatin is unstable in the acidic aqueous solution and will be easily decomposed into 3-Hydroxy-iso-compactin or pravastatin lactone or other impurities. During the extraction for the purification of pravastatin sodium, emulsion phenomena will also occur to deteriorate the product purity and quality. Therefore, the process of the prior art is not suitable for commercial mass production.

The present inventor has found the drawbacks of the prior art and invented the present process for stably purifying pravastatin sodium from a fermentation broth.

SUMMARY OF THE INVENTION

The object of the present invention is to provide a process for stably purifying pravastatin sodium comprising the steps of:

a. clarifying a fermentation broth containing pravastatin sodium by centrifugation or filtration to obtain a supernatant or filtrate containing the pravastatin sodium; and adjusting the supernatant or filtrate to be basic having pH value ranging from pH 10~13;

b. adsorbing the pravastatin sodium with non-ionic resin which is then washed with water; eluting the pravastatin sodium as adsorbed on the resin by water-soluble organic solvent to obtain pravastatin sodium fraction; and concentrating the fraction to be pravastatin sodium concentrate;

c. treating the concentrate with water-soluble anti-solvent or inorganic salt to form a precipitate of pravastatin sodium; and d. recrystallizing the precipitate for making pravastatin sodium crystal with high purity and high yield.

DETAILED DESCRIPTION

For isolation and adsorption of pravastatin sodium from a fermentation broth by non-ionic resin, it is found that the adsorption is very poor when the fermentation broth is placed in neutral condition.

The adsorption efficiency may be increased when the fermentation broth is adjusted to be acidic or basic. However, the pravastatin is unstable in acidic aqueous solution as aforementioned.

Surprisingly, the adsorption efficiency of pravastatin sodium on non-ionic resin will be greatly increased when the fermentation broth is adjusted to be basic ranging from pH 10~13, preferably ranging from pH 11~12 in accordance with the present invention.

For clarifying the fermentation broth, centrifugation or filtration is conducted to obtain a clear solution of supernatant or filtrate which is adjusted to be basic of pH 10~13.

The non-ionic resin is provided to adsorb the pravastatin sodium, which is then washed by water. Water-soluble organic solvent is provided to elute the pravastatin sodium on the resin to obtain pravastatin sodium fraction.

The non-ionic resin may be selected from Amberlite ®XA-D series, Diaion ®HP or SP series, but not limited in the present invention.

The adsorption of pravastatin sodium with non-ionic resin under basic condition in accordance with the present invention will overcome the drawbacks of instability of pravastatin when existing in acidic condition and the emulsion phenomena which occurs in conventional extraction process.

The pravastatin sodium as obtained through resin adsorption, water-wash and desorption steps of the present invention will render a high HPLC purity more than 93%, and a high yield more than 98%.

The HPLC detection parameters are shown as follows:

Mobile phase:Methanol:water:acetic acid:triethyl amine= 500:500:1:1

Column: Lichroshper RP-18e5.0 $\mu$, $\varnothing$4.0 mm×25 cm (Merck & Co.)

Column temperature: 40° C.

Flow rate: 1 ml/min

Detection wave length: UV: 238 nm

Under the basic condition (pH 11~12), the adsorption or desorption with non-ionic resin is performed in the present invention to obtain high purity and high yield of pravastatin sodium. Parallelly, the impurity of 6α-hydroxy-compactin sodium (epimer of pravastatin sodium) existing in the broth may be minimized, thereby increasing the overall purity and yield of the pravastatin sodium in accordance with the present invention. Such an epimer, having physical and chemical properties very similar to that of pravastatin, will not be easily removed by conventional crystallization, chromatography or even high performance liquid chromatography (HPLC).

However, due to the disclosure of the critical condition by adjusting the fermentation broth to be basic (pH 10~13, preferably pH 11~12) as disclosed in the present invention, the "obstacle" (the impurity epimer) hindering the mass production for purifying pravastatin sodium will be removed.

After resin adsorption, precipitation and crystallization may be applied to further purify the pravastatin sodium.

The eluant (with pravastatin sodium fraction) after the elution of the adsorption resin will be concentrated to obtain pravastatin sodium concentrate. And water-soluble anti-solvent is added into the concentrate for precipitation of pravastatin sodium. The addition of the anti-solvent will decrease the polarity of the concentrate and the pravastatin sodium is poorly soluble in such an anti-solvent, thereby accelerating the precipitation of the pravastatin sodium in the concentrate.

Or, an inorganic salt is added into the concentrate for salting-out the precipitate of pravastatin sodium.

Finally, crystallization or re-crystallization is conducted to obtain the pravastatin sodium with high purity.

During the elution of the adsorption resin, the water-soluble organic solvents may be selected from: methanol, acetone, or a mixture of methanol and acetone.

The water-soluble anti-solvents added into the concentrate for precipitation of pravartatin sodium may be selected from: ethanol, n-propanol, isopropanol, acetone and the mixture thereof. The acetone is most preferable.

The inorganic salts for salting out the pravastatin sodium precipitate may be selected from: ammonium sulfate, ammonium chloride, sodium sulfate, sodium chloride and potassium chloride. The sodium chloride is most preferable.

The present invention will be further described in detail in the following examples, which are provided to exemplify the invention, but not to limit the scope of the present invention.

EXAMPLE 1

A fermentation broth containing pravastatin sodium of 10 liters is centrifuged to remove microbial cell mass. The supernatant is added with 10 N sodium hydroxide solution to be basic of pH 12.0, which is then pumped at constant rate and loaded to a resin column of Diaion® HP-20 (¢ xH=5×60 cm; Bed vol=1.0L; S.V.=3.0). The resin is then washed with 7 liters of 0.1% (w/w) sodium hydroxide solution, and eluted with an eluant of 50% (w/w) methanol to obtain the pravastatin sodium elute. The elute is assayed by HPLC analysis to obtain crude pravastatin sodium with yield: 99.05% and purity: 94.0%.

The pravastatin sodium elute is adjusted to pH 9.0 by adding 3N hydrochloric acid therein, and further concentrated to 30% (w/w) pravastatin sodium by a concentrator under reduced pressure. The concentrate is added therein with 4.0 liters acetone and stirred for 4 hours at 25~30° C. It is continuously stirred for next 2 hours at cooling temperature of 0~5° C. to precipitate the pravastatin sodium. Vacuum filtration is done to obtain the filtered cake containing pravastatin sodium.

The filtered cake is slightly washed with little amount of acetone and dissolved in 120 ml water, added with 1.0 g activated carbon and stirred for 2 hours for decoloring. The solution is then filtered and the filtrate is concentrated to 25% (w/w) pravastatin sodium, 4.0 liters acetone is added into the concentrate and stirred under room temperature for 3 hours. Then, it is cooled to 0~5° C. and stirred for 2 hours to crystallize the pravastatin sodium, which is filtered under vacuum, dried to obtain purified pravastatin sodium: 18.3 g; overall yield: 61%; and purity: 98.5%.

EXAMPLE 2

A fermentation broth containing pravastatin sodium of 10 liters is centrifuged to remove microbial cell mass. The supernatant is added with 10 N sodium hydroxide solution to be basic of pH 11.0, which is then pumped at constant rate and loaded to a resin column of Amberlite® AD-16 (¢ xH=5×70 cm; Bed vol=1.2L; S.V.=3.0). The resin is then washed with 8 liters of 0.1% (w/w) sodium hydroxide solution, and eluted with an eluant of 50% (w/w) methanol to obtain the pravastatin sodium elute.

The pravastatin sodium elute is adjusted to pH 9.0 by adding 3N hydrochloric acid therein, and further concentrated to 3.0% (w/w) pravastatin sodium. The concentrate is added therein with 300 g sodium chloride and stirred for 4 hours at 25~30° C. It is continuously stirred for next 2 hours at cooling temperature of 0~5° C. to salt out the pravastatin sodium precipitate. Filtration is done to obtain the filtered cake containing pravastatin sodium, purity: 99.3%.

The salting-out cake is dissolved in 120 ml water, added with 1.0 g activated carbon and stirred for 2 hours for decoloring. The solution is then filtered and the filtrate is then desalted by XAD-4 or HP-20ss. The pravastatin sodium elute is concentrated under reduced pressure to 30% (w/w) and 4.0 liters acetone is added into the concentrate and stirred at 25~30° C. for 4 hours. Then, it is cooled to 0~5° C. and stirred for 2 hours to crystallize the pravastatin sodium, which is filtered under vacuum, dried to obtain purified pravastatin sodium: 16.5 g; overall yield: 55%; and purity: 99.5%.

EXAMPLE 3

A fermentation broth containing pravastatin sodium of 10 liters is centrifuged to remove microbial cell mass. The supernatant is added with 10 N sodium hydroxide solution to be basic of pH 11.0, which is then pumped at constant rate and loaded to a resin column of Diaion® SP-200 (¢ xH=5×60 cm; Bed vol=1.0L; S.V.=3.0). The resin is then washed with 7 liters of 0.1% (w/w) sodium hydroxide solution, and eluted with an eluant of 50% (w/w) methanol to obtain the pravastatin sodium elute. The elute is assayed by HPLC analysis to obtain crude pravastatin sodium with yield: 99% and purity: 95%.

The pravastatin sodium elute is adjusted to pH 9.0 by adding 3N hydrochloric acid therein, and further concentrated to 3.0% (w/w) pravastatin sodium by a concentrator under reduced pressure. The concentrate is added therein 280 g sodium chloride and stirred for 4 hours at 25~30° C. It is continuously stirred for next 2 hours at cooling temperature of 0~5° C. to precipitate the pravastatin sodium. Filtration is done to obtain the filtered cake containing pravastatin sodium.

The filtered cake is dissolved in 120 ml water, added with 1.2 g activated carbon and stirred for 2 hours for decoloring. The solution is then filtered and desalted by HP-20ss for de-salting. The pravastatin sodium elute is concentrated under reduced pressure to 30% (w/w) pravastatin sodium. 4.0 liters acetone is added into the concentrate and stirred at 25~30° C. for 4 hours. Then, it is cooled to 0~5° C. and stirred for 2 hours to crystallize the pravastatin sodium, which is filtered, dried to obtain purified pravastatin sodium: 17.0 g; overall yield: 56.7%; and purity: 99.6%.

EXAMPLE 4

A fermentation broth containing pravastatin sodium of 1000 liters is centrifuged to remove microbial cell mass. The supernatant is added with 45% (w/w) sodium hydroxide solution to be basic of pH 12.0, which is then pumped at constant rate and loaded to a resin column of Diaion® HP-20 (Bed vol=100L; S.V.=3.0). The resin is then washed with 800 liters of 0.1% (w/w) sodium hydroxide solution, and eluted with an eluant of 50% (w/w) methanol to obtain the pravastatin sodium elute. The elute is assayed by HPLC analysis to obtain crude pravastatin sodium with yield: 98.5% and purity: 94.5%.

The pravastatin sodium elute is adjusted to pH 9.0 by adding 6N hydrochloric acid therein, and further concentrated to 3.0% (w/w) pravastatin sodium. The concentrate is added therein with 30 kg sodium chloride and stirred for 4~6 hours at 25~30° C. It is continuously stirred for next 3 hours at cooling temperature of 0~5° C. to precipitate the pravastatin sodium. Centrifugation is done to obtain the filtered cake containing pravastatin sodium, purity: 99.4% by HPLC.

The filtered cake may be decolored, if necessarily. The cake is dissolved in 20 liters water and desalted by HP-20ss for de-salting. The pravastatin sodium elute is concentrated under reduced pressure to 30% (w/w) pravastatin sodium.

400 liters acetone is added into the concentrate and stirred at 25~30° C. for 4–6 hours. Then, it is cooled to 0~5° C. and stirred for 3 hours to crystallize the pravastatin sodium, which is filtered, dried to obtain purified pravastatin sodium: 1.68 kg; overall yield: 56%; and purity: 99.57%.

The present invention may produce pravastatin sodium with high purity and high yield. Unexpected impurities can be prevented in the purification process. Meanwhile, the solvents as used in the process are safe, not hazardous to the environment and the solvent consumption is controlled at a very reasonable rate. So, the present invention may be commercialized economically, without conflicting the environmental protection.

The present invention may be modified without departing from the spirit and scope of the present invention.

We claim:

1. A process for stably purifying pravastatin sodium comprising the steps of:
    a. clarifying a fermentation broth containing pravastatin sodium by a step selected from centrifugation and filtration to obtain a clear solution containing the pravastatin sodium; and adjusting the clear solution to be basic having pH value ranging from pH 10~13;
    b. adsorbing the pravastatin sodium with non-ionic resin which is then washed with water; eluting the pravastatin sodium as adsorbed on the resin by water-soluble organic solvent, which is selected from: methanol, acetone and a mixture of methanol and acetone, to obtain pravastatin sodium fraction; and concentrating the fraction to be pravastatin sodium concentrate;
    c. treating the concentrate to form a precipitate of pravastatin sodium; and
    d. recrystallizing the precipitate for making pravastatin sodium crystal with high purity and high yield.

2. A process according to claim 1, wherein the treating of said concentrate for forming a precipitate of pravastatin sodium in step (c) comprising the addition of water-soluble anti-solvent into said concentrate.

3. A process according to claim 2, wherein said water-soluble anti-solvent selected from: ethanol, n-propanol, isopropanol, acetone and the mixture thereof.

4. A process according to claim 1, wherein the treating of said concentrate for forming a precipitate of pravastatin sodium in step (c) comprising the addition of inorganic salt for salting out the pravastatin sodium precipitate.

5. A process according to claim 4, wherein said inorganic salt is selected form: ammonium sulfate, ammonium chloride, sodium sulfate, sodium chloride and potassium chloride.

* * * * *